(12) United States Patent  
Esnouf

(10) Patent No.: US 6,736,085 B1  
(45) Date of Patent: May 18, 2004

(54) HEAT CYCLE INDICATING DEVICE

(75) Inventor: Philip Stuart Esnouf, Toorak (AU)

(73) Assignee: Ultimate Medical Pty. Ltd., Richmond (AU)

( * ) Notice: Subject to any disclaimer, the term of this patent is extended or adjusted under 35 U.S.C. 154(b) by 0 days.

(21) Appl. No.: 09/926,545

(22) PCT Filed: May 17, 1999

(86) PCT No.: PCT/AU99/00370

§ 371 (c)(1),  
(2), (4) Date: Feb. 28, 2002

(87) PCT Pub. No.: WO99/60520

PCT Pub. Date: Nov. 25, 1999

(30) Foreign Application Priority Data

May 28, 1998 (AU) .............................................. PP3607

(51) Int. Cl.⁷ ................................................. G01K 1/02
(52) U.S. Cl. ........................ 116/216; 116/218; 116/221
(58) Field of Search ................................ 116/216, 221, 116/218

(56) References Cited

U.S. PATENT DOCUMENTS

| | | | |
|---|---|---|---|
| 1,637,050 A | * | 7/1927 | Rankin ........................ 116/216 |
| 5,018,874 A | | 5/1991 | Weynant née Girones .. 374/205 |
| 5,061,085 A | * | 10/1991 | Unfried et al. ............. 116/221 |
| 5,143,453 A | | 9/1992 | Weynant née Girones .. 374/205 |
| 5,313,935 A | | 5/1994 | Kortenbach et al. ........... 128/4 |
| 5,335,994 A | * | 8/1994 | Weynant nee Girones .. 116/216 |
| 5,359,993 A | | 11/1994 | Slater et al. .................... 128/4 |
| 5,452,335 A | | 9/1995 | Slater et al. .................. 377/25 |

FOREIGN PATENT DOCUMENTS

| EP | 0363289 B1 | 4/1990 |
|---|---|---|
| EP | 0581400 B1 | 2/1994 |

* cited by examiner

*Primary Examiner*—Christopher W. Fulton  
*Assistant Examiner*—Amanda J Hoolahan  
(74) *Attorney, Agent, or Firm*—Seed IP Law Group PLLC

(57) ABSTRACT

An indicating device for indicating the number of times in which a surgical fitting has been autoclaved, the device including a body which includes first and second sets of teeth and a bimetallic indexing ring having teeth thereon, the arrangement being such that on thermal expansion and contraction of the indexing ring, its teeth engage those of the body so as to rotate the ring in a step wise manner relative to the body so as to thereby indicate the number of heat cycles to which the indicating device has been subjected, the indexing ring being the only movable part of the device.

12 Claims, 9 Drawing Sheets

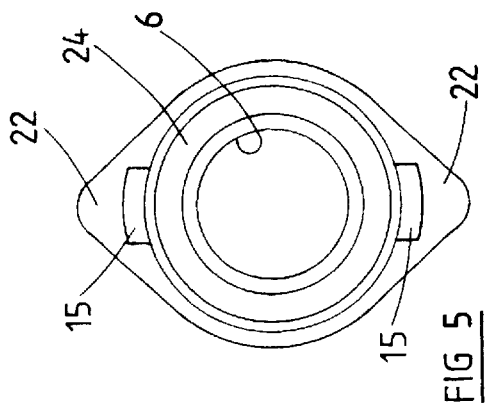
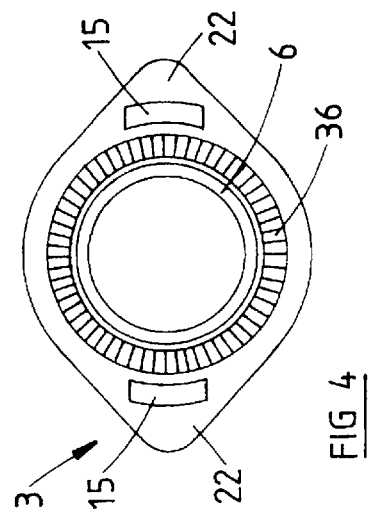
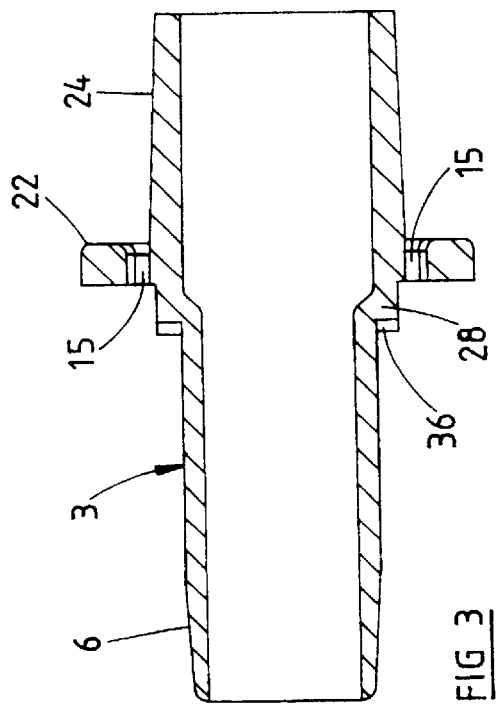
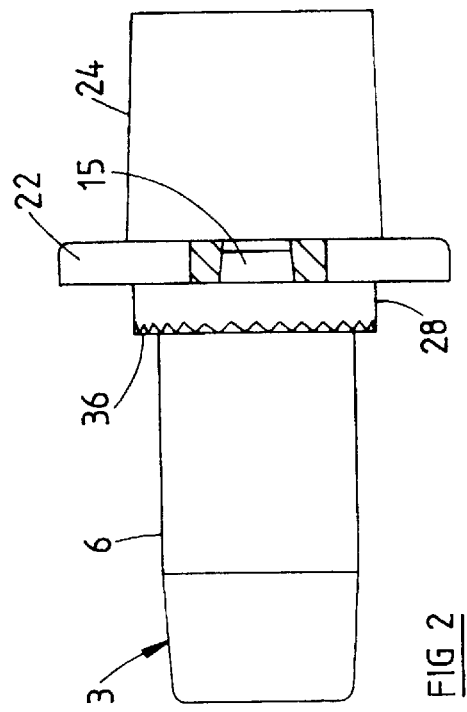

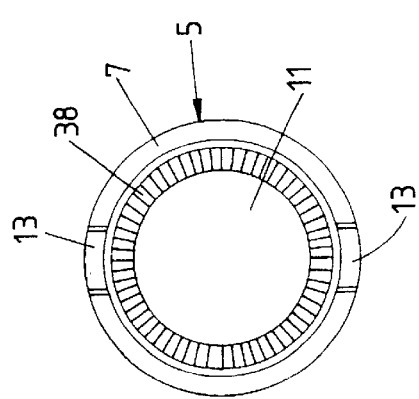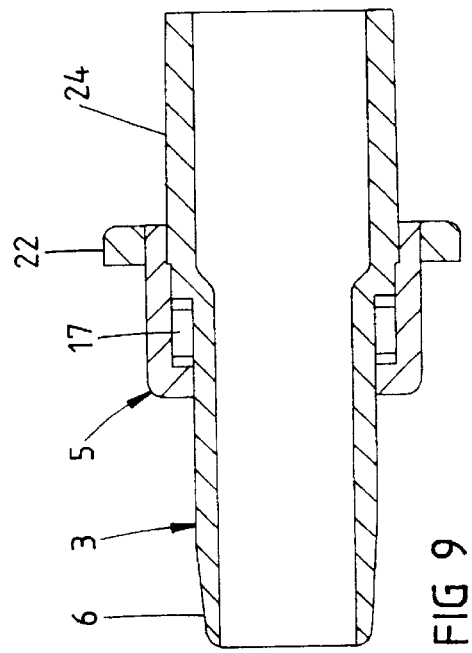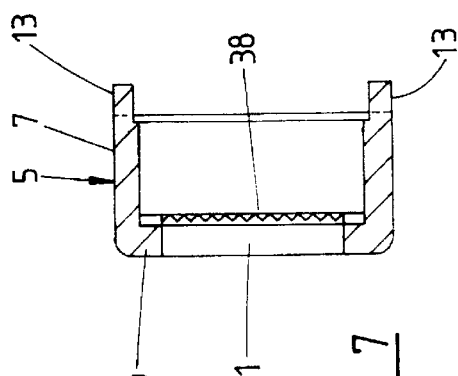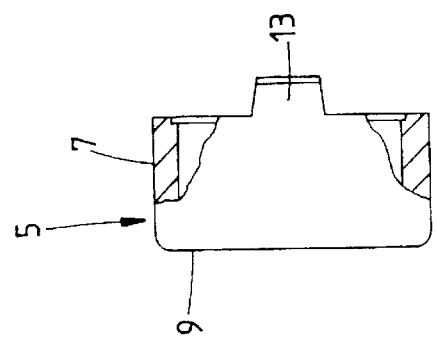

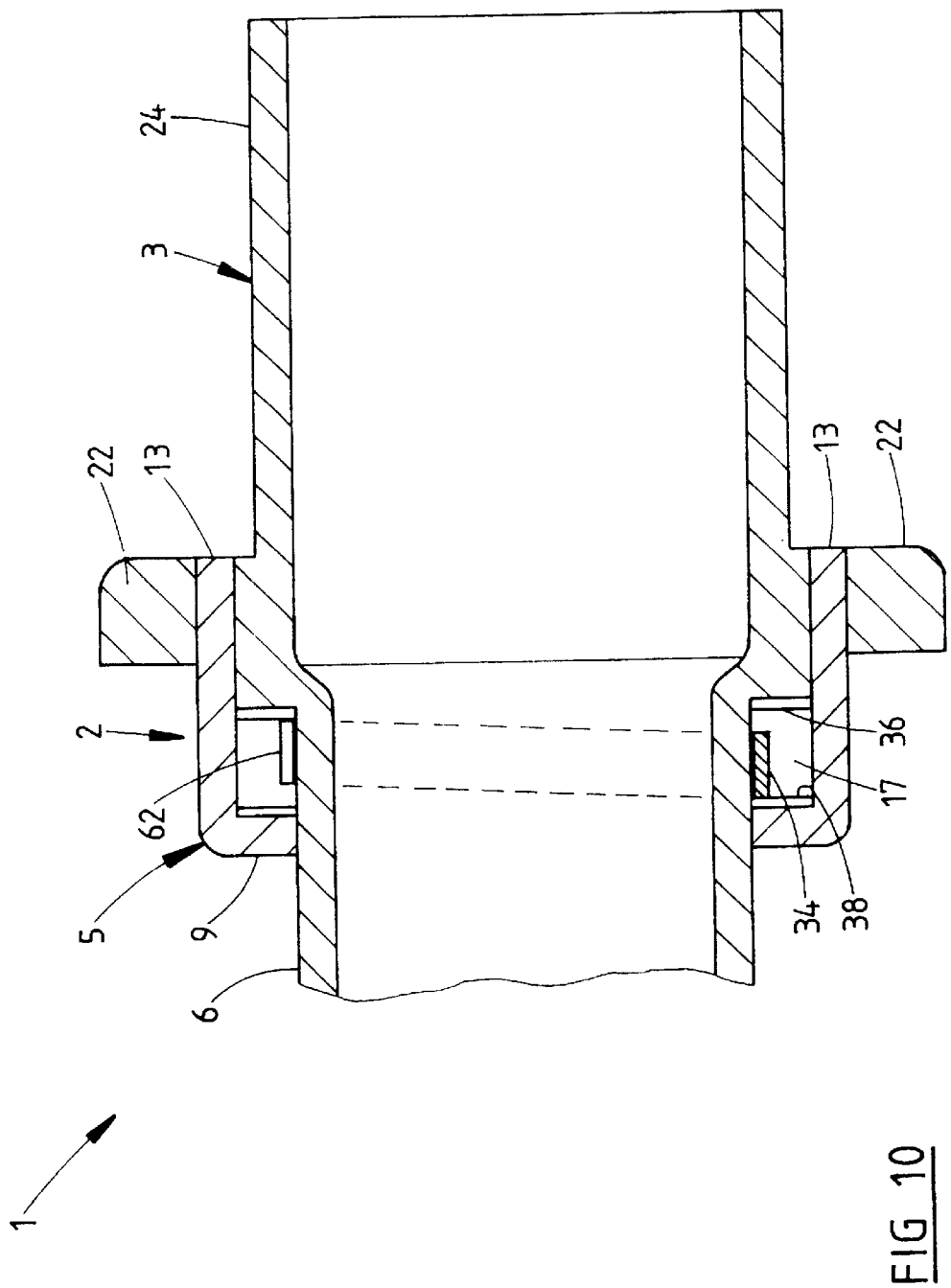

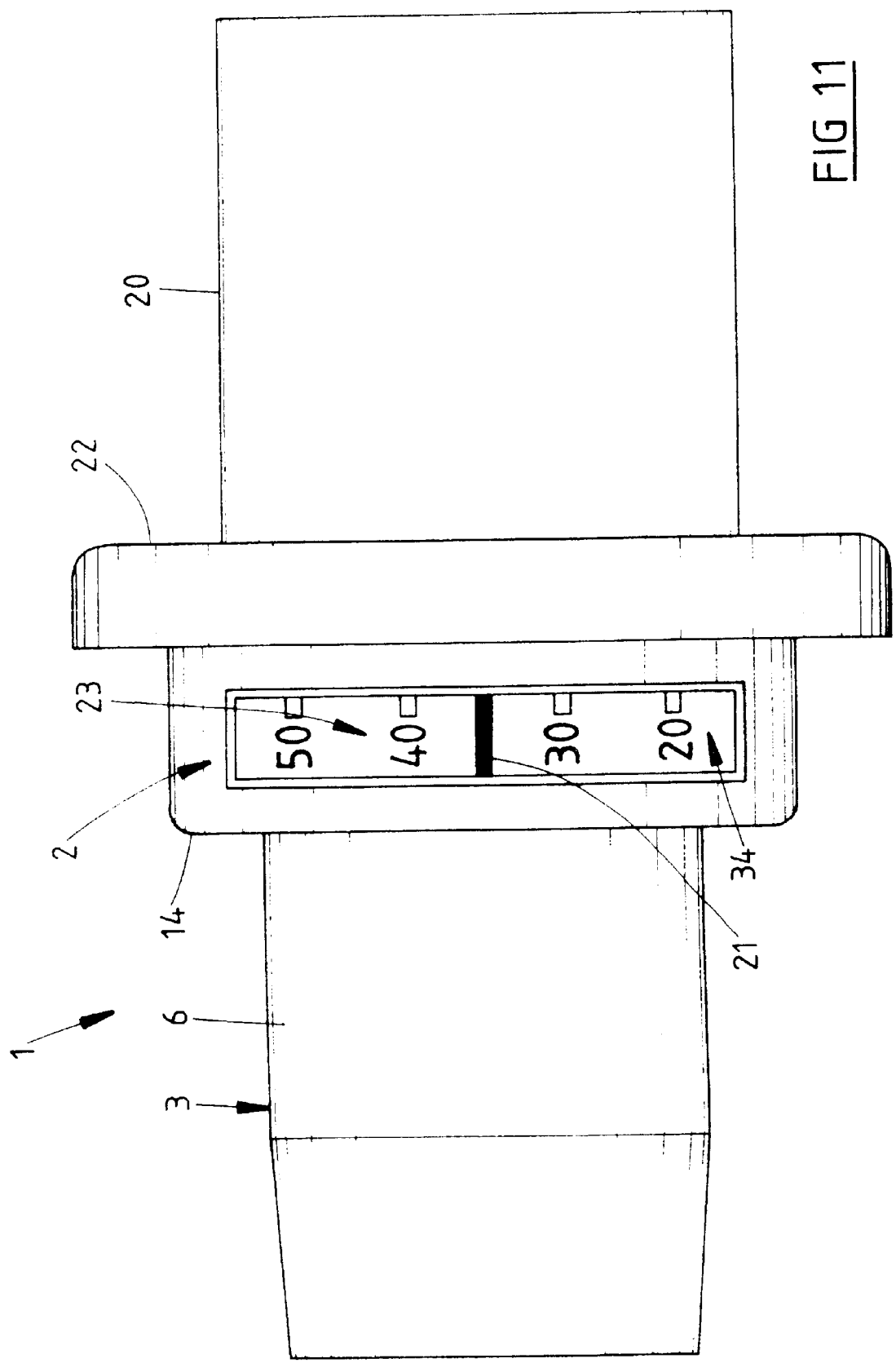

HEAT CYCLE INDICATING DEVICE

BACKGROUND OF THE INVENTION

This invention relates to a heat cycle indicating device.

1. Field of the Invention

More particularly, the invention relates to a heat cycle indicating device for indicating when the device has been subjected to a heat cycle above a predetermined temperature.

2. Description of the Related Art

Some articles are subjected to heat treatment in order to sterilise them. For instance, in the medical field non-disposable equipment is normally autoclaved after each use so that it can be reused. Sometimes the equipment to be autoclaved includes rubber and/or synthetic materials which can be safely autoclaved a limited number of times but when subjected to repeated heat cycling are prone to failure. Normally manufacturers of such equipment will specify the number of times which a particular article can be safely autoclaved before it is disposed of. In practice, however, it is sometimes difficult to accurately keep records of how many times a particular device or piece of equipment has been autoclaved.

It is known to provide in surgical equipment an indicator which indicates the number of times the device has been autoclaved. U.S. Pat. Nos. 5,313,935; 5,359,993and 5,452,335 disclose devices which have an indexing wheel which is acted upon by a bimetallic element. The arrangement is such that on heating and cooling of the device, the bimetallic element rotates the indexing wheel through one step to thereby indicate the number of times the device has been subjected to a heating cycle.

An object of the present invention is to provide an indicating device which is an improvement or simplification of the devices disclosed in the aforementioned patents.

BRIEF SUMMARY OF THE INVENTION

According to the present invention there is provided an indicating device for indicating heat cycling, said device including:
- a body including projections;
- an indexing element having indexing means the element being mounted for rotation relative to the body;
- the arrangement being such that on thermal expansion and contraction of the indexing element, the indexing means thereof engages said projections and cause a step rotation of the indexing element in one sense only relative to the body.

Preferred embodiments of the invention can be constructed in which the only moving part is the indexing element. This constitutes a significant simplification over known techniques and results in a cheaper product which is also more robust and reliable.

In accordance with the invention, the indicating device can be attached to or formed with the body as a surgical instrument or other piece of medical equipment which needs to be sterilised by autoclaving. Each time the equipment is autoclaved, the indexing means operates in association with indicating means so that when the number of safe autoclaving cycles has been reached, the appropriate staff will know that the equipment can no longer be safely used.

In one form of the invention, the indexing means may comprise an expansible ring having projections thereon which are engagable with complementary projections on a base member. During a heating and cooling cycle, the ring expands and is arranged to move relative to the body. Movement of the ring can be viewed relative to the body which may include markings which constitute part of the indicating means.

Preferably further, the ring is bimetallic and rotates about a cylindrical part of the body.

Preferably the indexing occurs after the device has experienced a predetermined temperature increase of 80° C. or more.

Preferably further, the body has associated therewith indexing teeth which are engagable with complementary teeth formed on the ring. In the preferred form of the invention, the ring is split and the trailing end of the ring includes a first projection which advances on the indexing teeth when the ring is heated and the leading edge is provided with a second tooth which advances to the next successive indexing tooth on cooling of the ring.

BRIEF DESCRIPTION OF THE DRAWINGS

The invention will now be further described with reference to the accompanying drawings, in which:

FIG. 2 is a side view of part of the connector;

FIG. 3 is a longitudinal cross-section through part of the connector;

FIGS. 4 and 5 are end views of part of the connector;

FIG. 6 is a side view of a collar part of the connector;

FIG. 7 is a cross-section through the collar part;

FIG. 8 is an end view of the collar part;

FIG. 9 is a longitudinal cross section through the connector;

FIG. 10 is an enlarged side view of the connector showing the indicating device in more detail;

FIG. 11 is a perspective view of the bimetallic ring; and

DETAILED DESCRIPTION OF THE INVENTION

Figure 1:
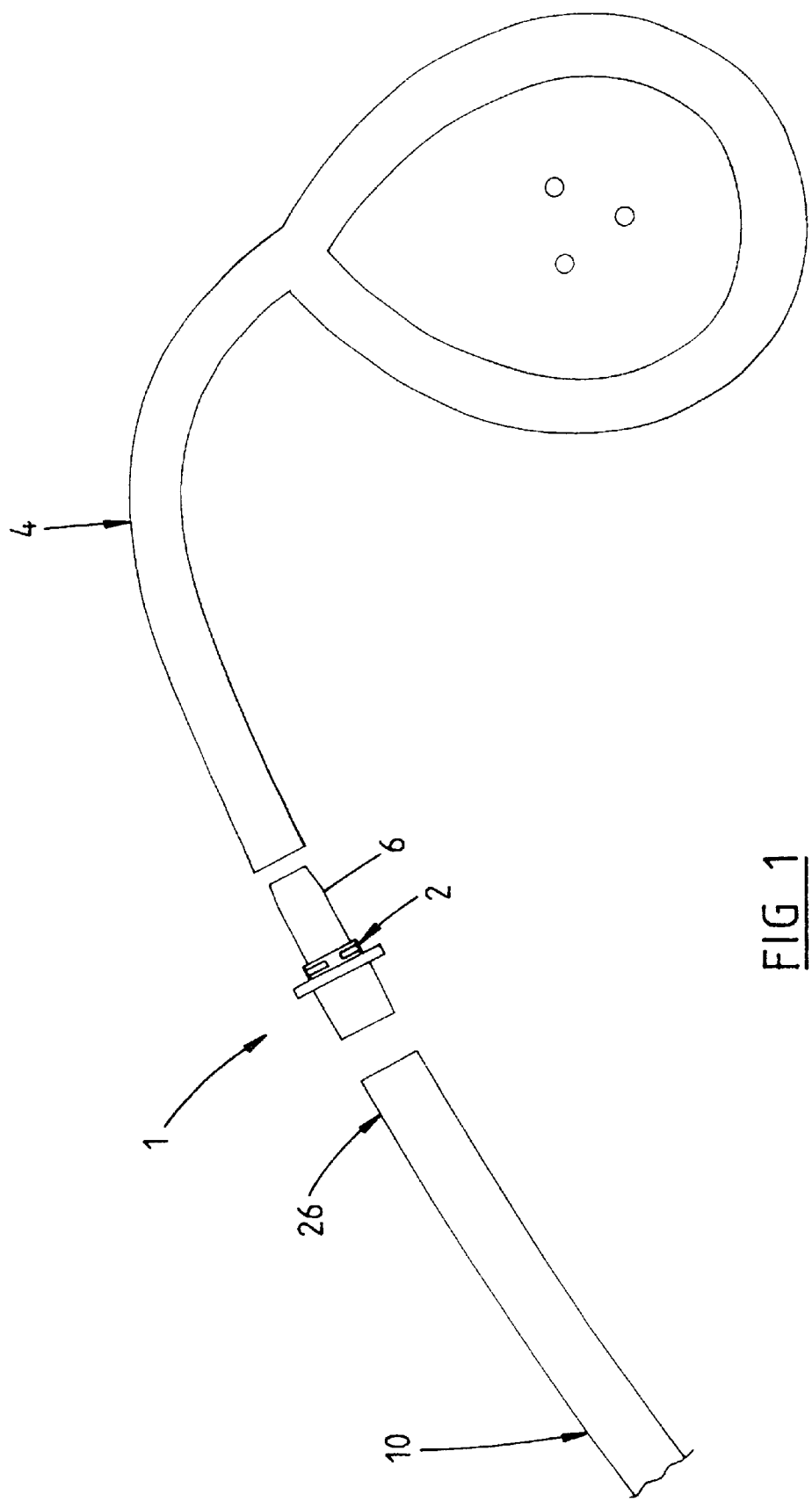
FIG. 1 is a schematic view of anaesthetic equipment having a surgical connector which incorporates the indicating device of the invention.

FIGS. 1 to 10 show a surgical connector 1 which is used to form a connection between a surgical device 4 such as a laryngeal mask and a tube 10 which is typically connected to a source of anaesthetic material. In accordance with the invention, the connector 1 incorporates an indicating device 2 which can be used to indicate the number of times to which the surgical device has been autoclaved. Many surgical devices have a limited number of times in which they can be safely autoclaved. This is typically 40 or 50. If the device is subjected to more autoclaving the materials making up the device can be subject to mechanical breakdown, thus making their use potentially unsafe. In accordance with the invention, medical staff can determine whether or not it is safe to reuse the surgical device simply by inspecting the indicating device 2.

The connector 1 is preferably moulded from transparent plastics material which is resistant to autoclaving temperatures. Such plastics material are known in the art and include high temperature stable polycarbonate plastics material such as high temperature Lexan (pholyphthalate carbonate), ULTEM (polyetherimide) or polysulphone plastics material (PSU).

The connector 1 is preferably moulded in two parts comprising a main body portion 3 which is shown in FIGS. 2 to 5 and a collar portion 5 which is shown in more detail in FIGS. 6, 7 and 8. The main body portion 3 is hollow so as to allow anaesthetic material to pass from the tube 10 into the laryngeal mask 4. One end is provided with a tapered socket 6 which can be inserted into the tube 10, in the usual way. The other end of the body 3 is formed with a socket 24 which is fixed to the laryngeal mask 4. The body 3 is provided with projecting wings 22 to facilitate handling of the connector 1. The body 3 includes an external shoulder 28 which has a first set of teeth 36 integrally moulded in the annular face of the shoulder, as best seen in FIGS. 2 and 4.

The collar 5 is shown in more detail in FIGS. 6, 7 and 8. It generally is in the form of a hollow cylindrical body having a cylindrical wall 7 and, at one end, an inwardly directed flange 9 having a bore 11 therein. On the annular internal face of the flange 9 is formed a second set of teeth 38, as best seen in FIGS. 7 and 8. The cylindrical wall 7 includes two projecting tabs 13.

FIG. 9 shows the collar 5 mounted on the body portion 3. It will be seen that the tapered socket 6 passes through the bore 11 of the collar and the tabs 13 enter into a pair of openings 15 which are formed in the wings 22. The collar 5 can be permanently connected to the body portion 3 by any suitable means such as mechanically interlocking, ultrasonic welding or adhesive solvent. As best seen in FIG. 9, an annular chamber 17 is formed between the body 3 and collar 5. More particularly, the inner and outer peripheries of the chamber 17 are formed by the socket 6 and cylindrical wall 7. The end walls of the chamber 17 are defined by the first and second sets of teeth 36 and 38.

Located within the chamber 17 is a ring 34, the ring 34 being inserted into the 30 chamber 17 prior to joining the collar 5 to the body 3.

The ring 34 is formed from a heat expansible material and on thermal expansion thereof is arranged to rotate relative to the connector 1 by engagement with the teeth 36 and 38, as will be described in more detail below. Because the collar 5 is formed from transparent material or at least includes a transparent window, a user can observe the position of the ring 34 relative to the connector body. The ring 34 is arranged to step or index through one incremental rotation during each autoclaving cycle. In this way provision can be made for indicating the number of times in which the connector 1 and its associated surgical device 4 have been autoclaved. The indication can be provided in a number of ways. For instance, the ring may include a circumferential gap which can be used to expose indicia formed in or printed on the exterior face of the socket 6 within the chamber 17. Alternatively, the ring 34 may include a reference mark 21, as shown in FIG. 11. The collar 5 may be moulded with or have printed thereon a count scale 23 and the reference mark 21 moves relative to the scale so as to also indicate the number of autoclaving cycles to which the device has been subjected.

The manner in which the ring 34 cooperates with the teeth 36 and 38 will now be described in more detail with reference to FIGS. 10, 12 and 13 to 15.

Figure 13:
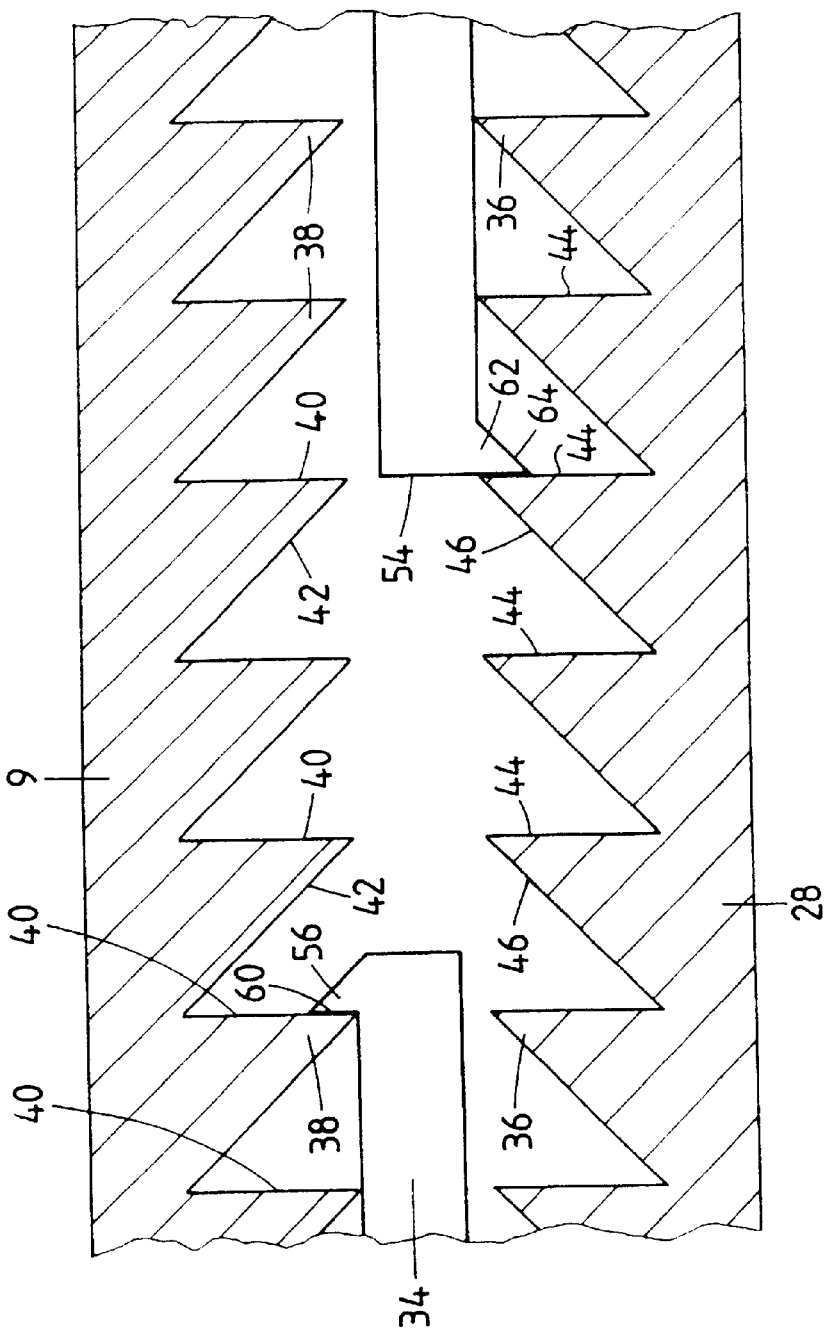

Each of the teeth 36 has a radial face 40 and an inclined face 42. Similarly, each of the teeth 38 has a radial face 44 and an inclined face 46. As seen in FIG. 13, the inclined faces 42 and 46 are inclined at equal and opposite angles relative to the indicating band 18. The radial faces 40 and 44 are adjacent to one another as shown in FIG. 13 but this is not essential to the invention.

Figure 12:
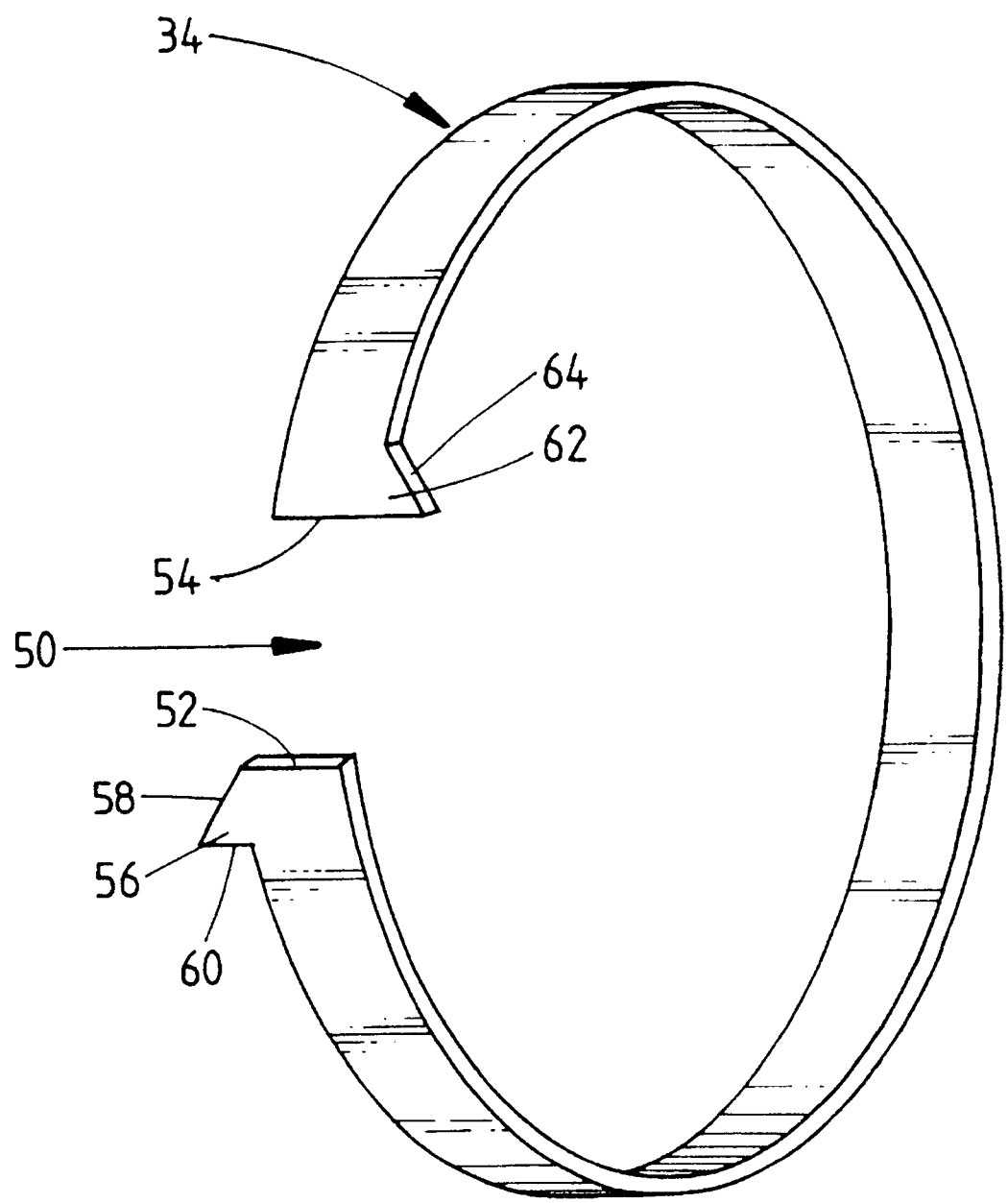
FIGS. 12, 13, 14 and 15 are diagrammatic representations illustrating the manner in which the indicating device functions.

The ring 34 is shown in more detail in FIG. 12. It includes a gap 50 which defines a leading edge 52 and a trailing edge 54. The leading edge 52 is formed with a laterally projecting leading edge tooth 56 formed with an inclined edge 58 and axial edge 60. The trailing edge 54 is formed with a trailing edge tooth 62 which projects in the opposite direction to the tooth 56. The tooth 62 includes an inclined edge 64 and the trailing edge 54 defines the rear edge of the tooth 62.

In the preferred form of the invention, the ring 34 is initially formed as a generally cylindrical ring with the gap 50 therein and then subjected to torsional deformation so that the ring 34 is helical and/or has roughly the shape of one coil or convolution of a helical spring. In this way the teeth 56 and 62 are biased in opposite axial directions, as will be explained below.

As mentioned above, the ring 34 is located within the chamber 17 and the width of the chamber is preferably such that the leading edge tooth 56 is biased into engagement with the teeth 38 whereas the trailing edge tooth 62 is biased into engagement with the teeth 36, as shown in FIG. 13. This biasing is caused by the torsional distortion of the ring as referred to above.

The ring 34 is preferably formed from a bimetallic material such as BHD 4700LE (the inside comprising an alloy of 19% nickel, 7% chrome and the balance iron, the outside comprising an alloy of 38% nickel, 7% chrome and the balance iron). A bimetallic material is preferred because the gap 50 enlarges when the ring is heated and contracts when the ring cools. Alternatively, a composite material from plastics material can be used such as epoxy/graphite or epoxy/glass, the fibre having a low coefficient of thermal expansion compared to the plastics material in which it is embedded so that it behaves like a bimetallic element. The fibre is preferably located on the outer circumference of the ring. A still further alternative would be to make the ring from two different plastics materials bonded together, each of the plastics materials having a different co-efficient of thermal expansion. A ring 34 of non-conductive material is suitable for use in Nuclear Magnetic Resonant Imaging (NMRI) equipment. Preferably the ring 34 undergoes significantly more expansion during an autoclave heating and cooling cycle than the plastics material from which the teeth 36 and 38 are moulded.

Figure 14:
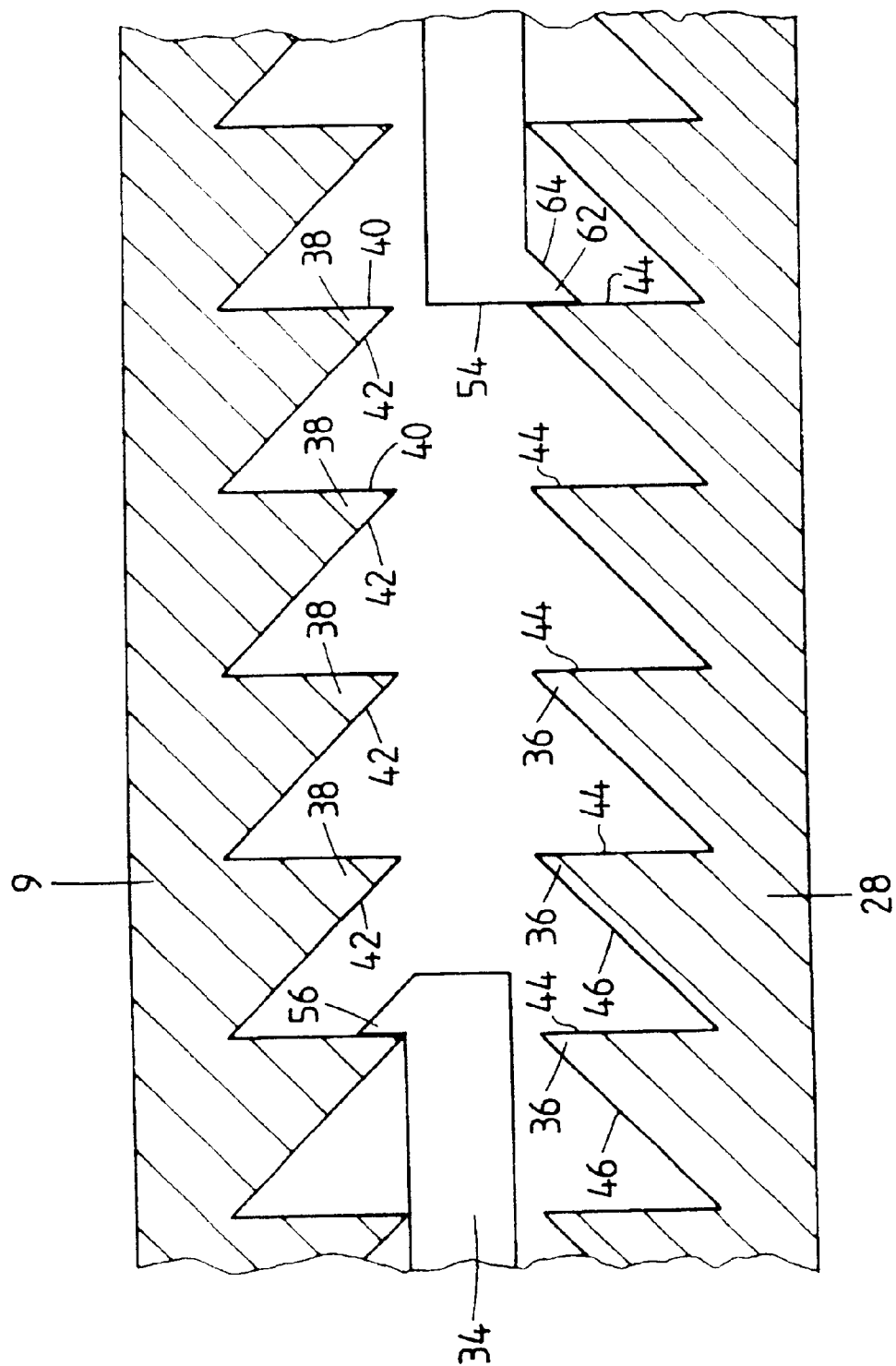

In the arrangement of the invention, when the device is subjected to heating the ring 34 will tend to expand accompanied with lengthening of the gap 50. When this occurs, the axial edge 60 of the leading edge tooth 56 will engage one of the teeth 38 and prevent any movement of the leading edge tooth 56 relative to the teeth 38. On the other hand, the inclined edge 64 of the trailing edge tooth 62 will slide over the inclined face 46 of the adjacent tooth 36. When expansion of the ring 34 has occurred sufficiently, on reaching a predetermined temperature, say 100° C. the trailing edge tooth 62 will pass the adjacent tooth 36 so that the trailing edge 54 of the ring will engage or lie adjacent to the radial face 44 of the tooth 36, as shown in FIG. 14.

Figure 15:
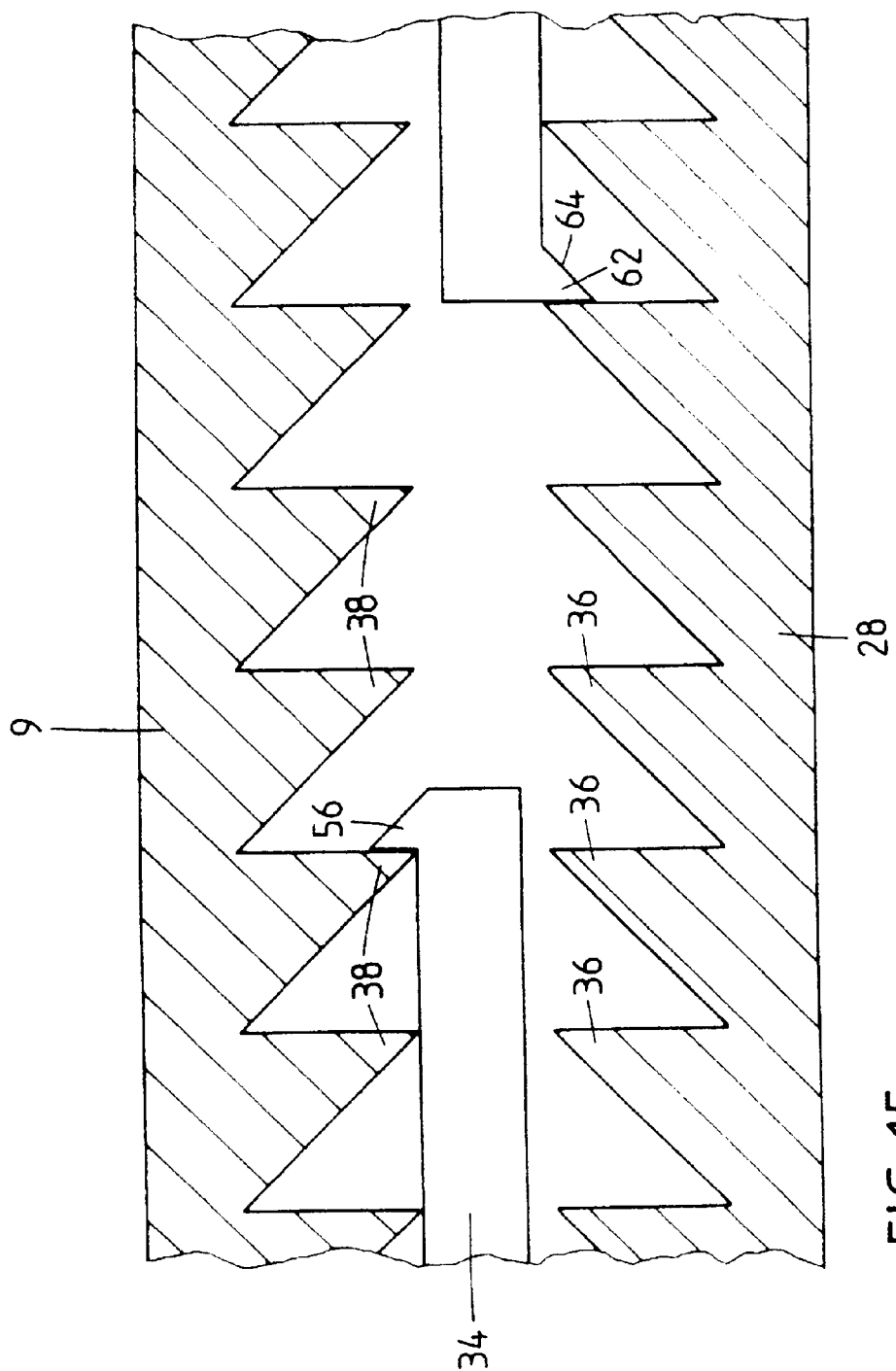

On cooling of the device, the ring 34 will cool and contract, the gap 50 tending to become shorter in length. When this happens, the trailing edge 54 of the ring will remain in engagement with the radial face 44 of one of the teeth 36. The leading edge tooth 56 will, however, be free to advance because its inclined edge 58 will be free to slide over the adjacent inclined face 42 of the tooth 38. This will occur when contraction has occurred to a predetermined level, say to room temperature or a temperature in the range 40° to 45°. Once contraction has occurred sufficiently, the trailing edge 54 of the leading edge tooth 56 will then lie adjacent to the radial face 40 of the tooth, as shown in FIG. 15. This prevents relative movement of the leading edge tooth 56 in a leftward direction as seen in FIG. 15. It will be appreciated that the heating and cooling cycle causes the ring 34 to move or be indexed through a rotational displacement equivalent to one pitch of the teeth 36 and 38.

During each autoclaving cycle the reference mark 21 will rotate an incremental step rotation equivalent to the pitch of the teeth 36 and 38. Thus the reference mark 21 moves relative to the scale 23 thereby providing the indication of the number of autoclaving cycles to which the equipment has been subjected. Similarly, if an indicating band (not shown) were provided on the spigot 6, it could be observed through the gap 50 in the ring 34 so as to similarly provide an indication of the number of autoclaving cycles.

In a prototype of the connector 1, there are fifty-nine teeth 36 and the same number of teeth 38. The width of the ring 34 is about 4 mm (as measured in an axial direction).

It will be appreciated by those skilled in the art that the principles of the invention can be applied to any equipment which is subjected to heating and cooling cycles. More particularly, the invention would have application in all forms of surgical equipment, anaesthetic equipment, dental equipment and/or veterinary equipment.

Many modifications will be apparent to those skilled in the art without departing from the spirit and scope of the invention.

I claim:

1. An indicating device for indicating heat cycling, said device including:
    a body including projections in the form of first and second sets of teeth;
    an indexing element having indexing means for engagement with the first and second sets of teeth, the element being mounted for rotation relative to the body, such that on thermal expansion and contraction of the indexing element, the indexing means thereof engages said projections to cause a step rotation of the indexing element in one sense only relative to the body;
    wherein the first and second sets of teeth are located in spaced planes which are perpendicular to an axis of rotation of the indexing element and the indexing means includes a trailing edge tooth and a leading edge tooth which are respectively engagable with the first and second sets of teeth, the trailing edge tooth including an inclined edge and an axial edge, each tooth of the first set of teeth including an inclined face and a radial face, the leading edge tooth including an inclined edge and an axial edge and each tooth of the second set of teeth including an inclined face and a radial face, arranged whereby:
        (i) on thermal expansion of the indexing element, the axial edge of the leading edge tooth abuts the radial face of one of the teeth of the second set of teeth and the inclined edge of the trailing edge tooth fully slides over the inclined face of one of the teeth of the first set of teeth until the axial face of the trailing edge tooth at least partly lies adjacent to the radial face of said one tooth of the first set of teeth; and
        (ii) on thermal contraction of the indexing element the axial face of the trailing edge tooth abuts the radial face of said one tooth of the first set of teeth and the inclined edge of the leading edge tooth fully slides over the inclined face of a next upstream tooth, relative to the sense of rotation of the indexing element of the second set of teeth, until the axial face of the leading edge tooth at least partly lies adjacent to the radial face of said next upstream tooth,
    such that on thermal expansion and contraction, the indexing element is rotated by an amount corresponding to a pitch of the first and second sets of teeth.

2. An indicating device as claimed in claim 1 wherein the indexing element is in the form of a ring.

3. An indicating device as claimed in claim 1 wherein the only moving part is the indexing element.

4. An indicating device as claimed in claim 1 wherein the indexing element is bimetallic.

5. An indicating device as claimed in claim 1 wherein the body includes first indicia and the indexing means includes indicating means, the arrangement being such that the indicating means advances relative to said indicia during each step rotation thereof so as to indicate the number of times the device has been subjected to a heat cycle.

6. An indicating device as claimed in claim 1 wherein the body comprises a surgical fitting moulded from autoclaveable plastics material.

7. An indicating device as claimed in claim 6 wherein the fitting includes a socket and the indexing element is mounted coaxially about the socket.

8. An indicating device as claimed in claim 2 wherein the indexing element includes a gap and is formed such that on thermal expansion thereof the gap increases, as measured in a circumferential direction.

9. An indicating device as claimed in claim 8 wherein the trailing edge tooth and the leading edge tooth are located adjacent to said gap.

10. An indicating device as claimed in claim 9 wherein the trailing edge tooth and the leading edge tooth project in axial directions in opposite senses.

11. An indicating device as claimed in claim 10 wherein the indexing element is made of resilient material and is arranged to bias the trailing edge tooth into resilient engagement with the teeth of the first set of teeth and the leading edge tooth into resilient engagement with the teeth of the second set of teeth.

12. An indicating device as claimed in claim 11 wherein the indexing element has substantially the form of one convolution of a helix.

* * * * *

UNITED STATES PATENT AND TRADEMARK OFFICE
CERTIFICATE OF CORRECTION

PATENT NO. : 6,736,085 B1
DATED : May 18, 2004
INVENTOR(S) : Philip Stuart Esnouf It is certified that error appears in the above-identified patent and that said Letters Patent is hereby corrected as shown below:

<u>Title page,</u>
Item [30], Foreign Application Priority Data, "May 28, 1998" should read -- May 20, 1998 --.

Signed and Sealed this

Third Day of January, 2006

JON W. DUDAS
*Director of the United States Patent and Trademark Office*